United States Patent
Kasama

(10) Patent No.: US 8,827,916 B2
(45) Date of Patent: Sep. 9, 2014

(54) ELECTRONIC DEVICE AND PULSE RATE CALCULATING METHOD

(71) Applicant: Fujitsu Limited, Kawasaki (JP)

(72) Inventor: Koichiro Kasama, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 65 days.

(21) Appl. No.: 13/715,663

(22) Filed: Dec. 14, 2012

(65) Prior Publication Data

US 2013/0102911 A1    Apr. 25, 2013

Related U.S. Application Data

(62) Division of application No. 12/320,531, filed on Jan. 28, 2009, now Pat. No. 8,357,098.

(30) Foreign Application Priority Data

Jun. 12, 2008    (JP) ................................. 2008-153637

(51) Int. Cl.
- *A61B 5/02*    (2006.01)
- *A61B 5/22*    (2006.01)
- *A61B 5/024*    (2006.01)
- *A61B 5/0255*    (2006.01)

(52) U.S. Cl.
CPC ............... *A61B 5/0255* (2013.01); *A61B 5/22* (2013.01); *A61B 5/02416* (2013.01); *A61B 5/02438* (2013.01); *A61B 2560/0462* (2013.01)
USPC ...................................................... 600/500

(58) Field of Classification Search
USPC .................................. 600/481, 500; 482/8
See application file for complete search history.

(56) References Cited

U.S. PATENT DOCUMENTS

| 6,547,728 B1 | 4/2003 | Cornuejois |
| 2003/0028116 A1* | 2/2003 | Bimbaum ................. 600/500 |

FOREIGN PATENT DOCUMENTS

| JP | 57-142238 | 9/1982 |
| JP | 64-49538 | 2/1989 |
| JP | 5-184548 | 7/1993 |
| JP | 10-295658 | 11/1998 |
| JP | 2003-164430 | 6/2003 |

OTHER PUBLICATIONS

"Heart Beat Counter Model PL-6000", http://www.cateye.co.jp/echtml/pl6000.html, Search on Jun. 4, 2008.
Patent Abstracts of Japan, Publication No. 64-049538, Published Feb. 27, 1989.

(Continued)

*Primary Examiner* — Michael D'Angelo
*Assistant Examiner* — Christian Jang
(74) *Attorney, Agent, or Firm* — Staas & Halsey LLP

(57) ABSTRACT

In an electronic device, a pulse rate measuring unit measures user's pulse rate. For example, the pulse rate measuring unit obtains a change in blood flow from a light passing through a user's fingertip, and measures user's current pulse rate based on it. A pulse rate memory unit has previously stored user's previous pulse rate. A pulse rate calculator calculates the user's pulse rate while changing a ratio of the user's current pulse rate measured by the pulse rate measuring unit to the user's previous pulse rate previously stored in the pulse rate memory unit after starting to measure the user's pulse rate. The user's pulse rate calculated by the pulse rate calculator is displayed as the user's pulse rate on a display unit.

1 Claim, 12 Drawing Sheets

(56) References Cited

OTHER PUBLICATIONS

Patent Abstracts of Japan, Publication No. 10-295658, Published Nov. 10, 1998.
Patent Abstracts of Japan, Publication No. 05-184548, Published Jul. 27, 1993.
Patent Abstracts of Japan, Publication No. 2003-164430, Published Jun. 10, 2003.
Japanese Patent Office Action issued in Japanese Patent Application No. 2008-153637 dated Oct. 2, 2012.
Office Action (Notice of Allowability) mailed Oct. 24, 2012 in U.S. Appl. No. 12/320,531.
Notice of Allowance mailed Sep. 21, 2012 in U.S. Appl. No. 12/320,531.
Office Action mailed Feb. 10, 2012 in U.S. Appl. No. 12/320,531.
Office Action (Restriction Requirement) mailed Dec. 1, 2012 in U.S. Appl. No. 12/320,531.
U.S. Appl. No. 12/320,531, filed Jan. 28, 2009, Koichiro Kasama, Fujitsu Limited.

* cited by examiner

EXERCISE
INTENSITY TB
25

| EXERCISE INTENSITY (METs) | COEFFICIENT |
|---|---|
| 1.0 – | 1.00 |
| 1.5 – | 1.25 |
| 2.0 – | 1.35 |
| 2.5 – | 1.45 |
| 3.0 – | 1.55 |
| 5.0 – | 1.65 |
| 7.0 – | 1.75 |
| 10.0 – | 1.85 |

FIG. 7

|  | Pr | : | P' |
|---|---|---|---|
| 1 sec. (n=1) | 1 | : | 9 |
| 2 sec. (n=2) | 2 | : | 8 |
| 3 sec. (n=3) | 3 | : | 7 |
| ⋮ |  | ⋮ |  |
| 10 sec. (n=10) | 10 | : | 0 |

FIG. 8

| TIME OF DISPLAY | 1st TIME | 2nd TIME | 3rd TIME | 4th TIME | |
|---|---|---|---|---|---|
| MEASURED PULSE RATE | 80 | 90 | 99 | 100 | ⋮ |
| CORRECTED PULSE RATE | 80 | 85=(80+90)/2 | 92=(85+99)/2 | 100 | ⋮ |
| DISPLAYED PULSE RATE | 80 | 85 | 92 | 100 | ⋮ |

FIG. 11

ELECTRONIC DEVICE AND PULSE RATE CALCULATING METHOD

CROSS-REFERENCE TO RELATED APPLICATIONS

This application is a Divisional of application Ser. No. 12/320,531 filed Jan. 28, 2009, now U.S. Pat. No. 8,357,098, and is based upon and claims the benefit of priority of the prior Japanese Patent Application No. 2008-153637, filed on Jun. 12, 2008, the entire contents of which are incorporated herein by reference.

FIELD

The embodiments discussed herein are related to an electronic device and a pulse rate calculating method.

BACKGROUND

There are various kinds of conventional pulse meters available, one of which is designed to have a pulse sensor to be attached to one of user's ears to measure his pulse rate and display the measured pulse rate on a display unit.

Some pulse meters are capable of displaying user's pulse rate in real time immediately after starting to measure the pulse.

However, it takes a predetermined period of time for these conventional pulse meters to display a reliable pulse rate after the pulse rate measurement is started. This means that the pulse meters may not display a pulse rate with high accuracy immediately after starting to measure the pulse rate.

SUMMARY

According to an aspect of the embodiments, an electronic device for displaying user's pulse rate includes: a pulse rate measuring unit configured to measure user's current pulse rate; a pulse rate memory unit configured to store user's previous pulse rate; and a pulse rate calculator configured to calculate the user's pulse rate while changing a ratio of the user's current pulse rate measured by the pulse rate measuring unit to the user's previous pulse rate stored in the pulse rate memory unit.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 7 illustrates an example data structure of an exercise intensity TB;
FIG. 8 is a diagram explaining a user's pulse rate to be displayed on a display unit of the electronic device;
FIG. 11 is a diagram explaining how to correct a pulse rate according to the third embodiment.

DESCRIPTION OF EMBODIMENT(S)

Figure 1:
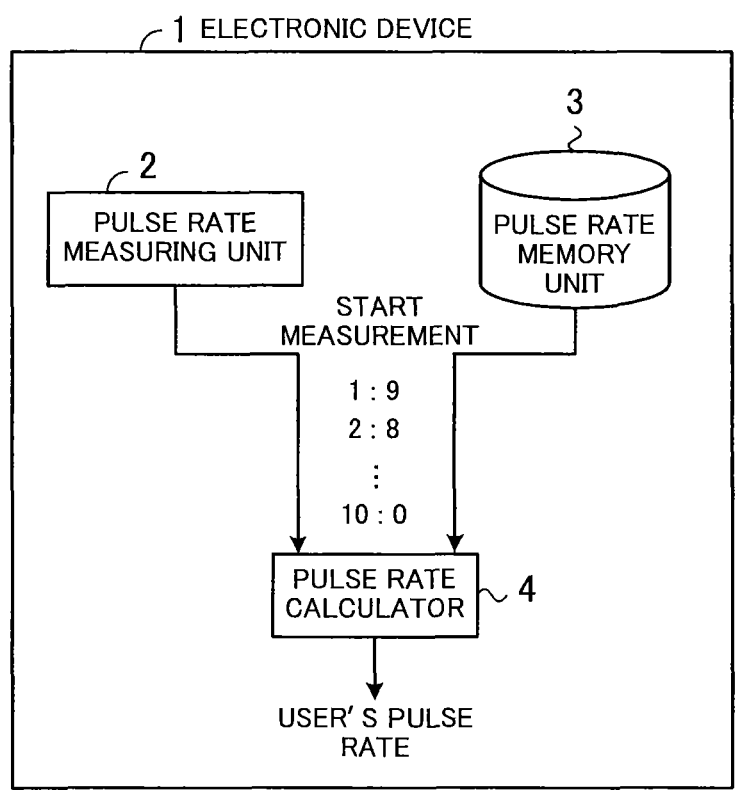
FIG. 1 illustrates the outline of an electronic device.

Preferred embodiments of the present invention will be explained below with reference to the accompanying drawings, wherein like reference numerals refer to like elements throughout.

FIG. 1 illustrates the outline of an electronic device. As illustrated in FIG. 1, the electronic device 1 has a pulse rate measuring unit 2, a pulse rate memory unit 3, and a pulse rate calculator 4.

The pulse rate measuring unit 2 measures user's current pulse rate. For example, the pulse rate measuring unit 2 obtains a change in blood flow from light passing through a user's fingertip, and measures the user's current pulse rate based on it.

The pulse rate memory unit 3 has previously stored user's previous pulse rate.

After starting to measure user's pulse rate, the pulse rate calculator 4 calculates the user's pulse rate while changing a ratio of the user's current pulse rate measured by the pulse rate measuring unit 2 to the user's previous pulse rate stored in the pulse rate memory unit 3. The user's pulse rate calculated by the pulse rate calculator 4 is displayed on a display unit.

For example, when starting to measure user's pulse rate, the pulse rate calculator 4 calculates the user's pulse rate by setting a ratio of the user's current pulse rate measured by the pulse rate measuring unit 2 to the user's previous pulse rate stored in the pulse rate memory unit 3 to 1:9. Then, the pulse rate calculator 4 changes the ratio to 2:8, and calculates the user's pulse rate. After that, similarly, the pulse rate calculator 4 calculates the user's pulse rate while changing the ratio until the ratio is set to 10:0. Thereafter, the pulse rate calculator 4 uses only the user's current pulse rate (at the ratio of 10) measured by the pulse rate measuring unit 2 as the user's pulse rate.

That is, while the pulse rate measuring unit 2 may not obtain a pulse rate with high accuracy immediately after starting to measure the pulse rate, the pulse rate calculator 4 calculates user's pulse rate by setting high the ratio of the user's previous pulse rate stored in the pulse rate memory unit 3. In the subsequent calculations of the user's pulse rate, the more accurate pulse rate the pulse rate measuring unit 2 calculates, the higher the pulse rate calculator 4 sets the ratio of the user's current pulse rate measured by the pulse rate measuring unit 2.

As described above, when starting to measure user's pulse rate, the electronic device 1 calculates the user's pulse rate while changing a ratio of user's current pulse rate measured by the pulse rate measuring unit 2 to user's previous pulse rate stored in the pulse rate memory unit 3. This makes it possible to display a pulse rate with high accuracy immediately after the pulse rate measurement is started.

Now, the first embodiment will be described with reference to the accompanying drawings.

Figure 2:
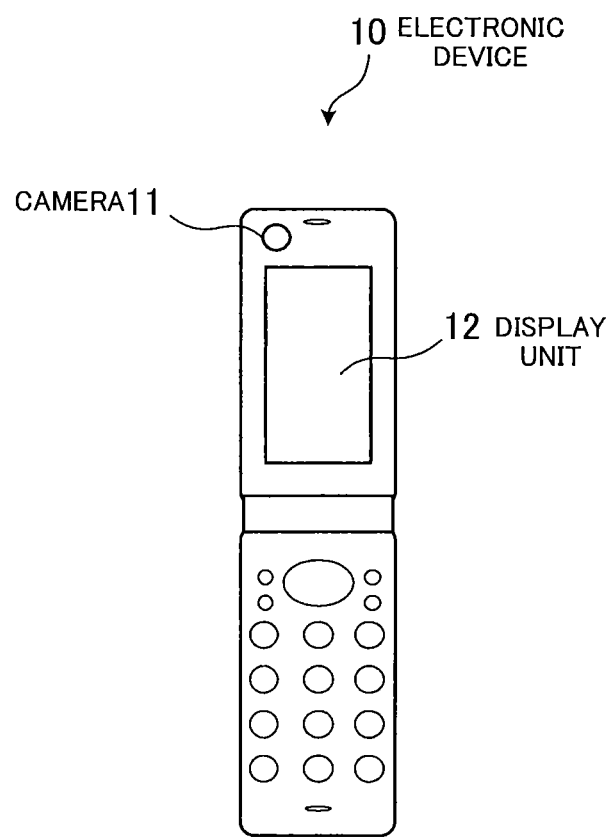
FIG. 2 illustrates an electronic device according to the first embodiment.

FIG. 2 illustrates an electronic device according to the first embodiment. As illustrated in FIG. 2, the electronic device 10 has a camera 11 and a display unit 12. For example, the camera 11 is a Complementary Metal Oxide Semiconductor (CMOS) image sensor, and the display unit 12 is a Liquid Crystal Display (LCD). The electronic device 10 is a mobile telephone, for example.

The user can easily measure his pulse rate by using the electronic device 10 while doing exercise such as walking or jogging. The user can measure the pulse rate by placing his fingertip on the camera 11 of the electronic device 10. The pulse rate is displayed on the display unit 12 of the electronic device 10. However, the user needs to previously measure and store his pulse rate at rest in the electronic device 10.

The electronic device 10 begins to display user's pulse rate on the display unit 12 immediately after the user places his fingertip on the camera 11. The electronic device 10 calculates and displays the pulse rate with high accuracy by using the previously stored pulse rate at rest on the display unit 12 immediately after starting to measure the pulse rate. This allows the user to know his pulse rate with high accuracy immediately after starting the pulse rate measurement.

Figure 3:
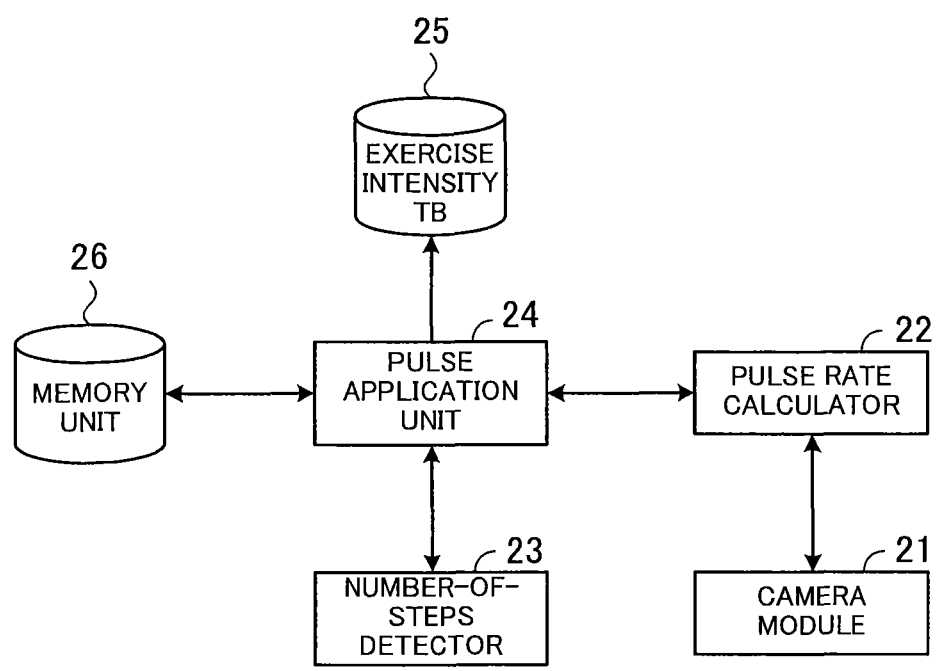
FIG. 3 is a block configuration diagram of the electronic device of FIG. 2.

FIG. 3 is a block diagram of the electronic device of FIG. 2. As illustrated in FIG. 3, the electronic device 10 has a camera module 21, a pulse rate calculator 22, a number-of-steps detector 23, a pulse application unit 24, an exercise intensity table (TB) 25, and a memory unit 26. Each unit in FIG. 3 is realized by a Central Processing Unit (CPU) executing a pulse rate calculating program stored in a memory, for example.

Upon reception of a camera drive mode request from the pulse application unit 24, the camera module 21 activates the camera 11 based on preset camera setting.

The camera setting includes a frame rate, an auto white balance, automatic luminance adjustment, and a data capture format, for example. More specifically, the camera module 21 sets the frame rate of the camera 11 to 12 fps (frames per second), sets the auto white balance off, sets the automatic luminance adjustment on, and sets an output format of image data to YUV format. The camera module 21 outputs image data received from the camera 11 to the pulse rate calculator 22.

The pulse rate calculator 22 calculates a change in blood flow of the user's fingertip placed on the camera 11, based on the image data received from the camera module 21.

In general, light is absorbed into hemoglobin. Therefore, the luminance of light passing through a human body such as fingers becomes smaller as a blood flow is higher, and vise versa. Therefore, the pulse rate calculator 22 is capable of calculating a change in user's blood flow based on the luminance information of the image data output from the camera module 21. More specifically, the pulse rate calculator 22 calculates the change in blood flow from a change in luminance information (Y information) of the image data in YUV format output from the camera module 21.

If the luminance information is equal to or greater than a predetermined threshold value, the pulse rate calculator 22 determines that there is no fingertip on the camera 11, and therefore does not calculate a change in blood flow.

The pulse rate calculator 22 calculates a maximum value or a minimum value from the change in blood flow calculated from the image data, and takes the calculated maximum value or minimum value as a pulse rate.

Figure 4:
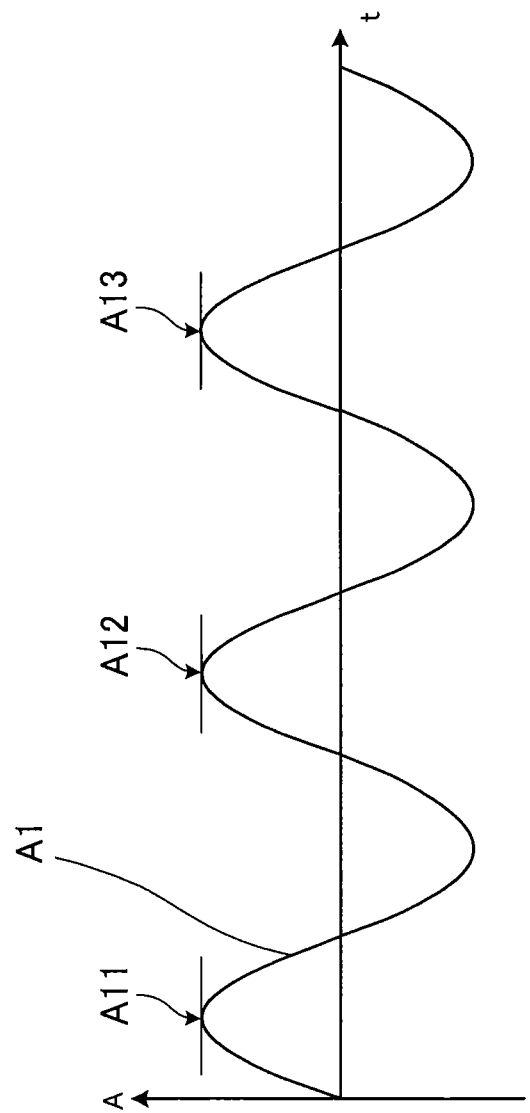
FIG. 4 is a diagram explaining a change in blood flow and a pulse rate.

FIG. 4 is a diagram explaining a change in blood flow and a pulse rate. A waveform A1 illustrated in FIG. 4 represents a change in blood flow calculated by the pulse rate calculator 22. The horizontal axis in FIG. 4 indicates time while the vertical axis indicates amplitude (A) of blood flow. The change in blood flow represented by the waveform A1 is illustrated to have a sine wave for explanation.

The pulse rate calculator 22 calculates a change in blood flow represented by the waveform A1 of FIG. 4 based on the image data output from the camera module 21. Then, the pulse rate calculator 22 calculates the maximum value of the waveform A1 indicated by arrows A11 to A13, and takes it as a pulse (pulse beat). That is, the maximum value indicated by the arrows A11 to A13 in FIG. 4 is taken as user's pulse.

The maximum value of the waveform A1 can be obtained by differentiating the waveform A1 once and twice. If values obtained by differentiating the waveform A1 once and twice are "0" and "negative value", respectively, the point can be taken as the maximum value.

It should be noted that a pulse can be obtained from the minimum value in the same way. For example, if values obtained by differentiating the waveform A1 once and twice are "0" and "positive value", respectively, the point can be taken as the minimum value. The pulse rate calculator 22 can take the minimum value as a pulse.

The pulse rate calculator 22 creates a histogram of peak-to-peak intervals (pulse beats) within a predetermined period of time (window) including the calculated maximum value (hereinafter, this may be called peak). For example, the pulse rate calculator 22 creates a histogram of peak-to-peak intervals for a window covering seconds. It should be noted that the pulse rate calculator 22 can creates a histogram of peak-to-peak intervals from the minimum value.

Figure 5:
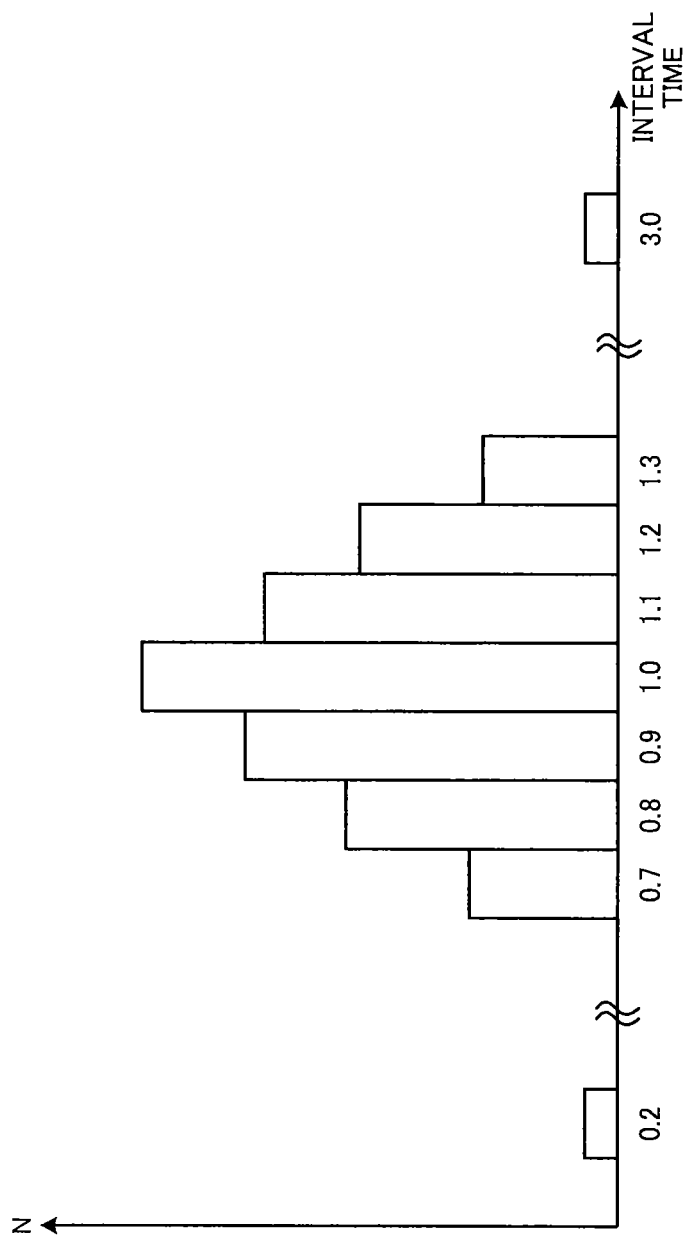
FIG. 5 is a diagram explaining a histogram.

FIG. 5 is a diagram explaining a histogram. The pulse rate calculator 22 creates a histogram of peak-to-peak intervals, as illustrated in FIG. 5, from the 20-second window of the waveform A1 of FIG. 4, for example. That is, the pulse rate calculator 22 creates the histogram of peak-to-peak intervals representing a change in blood flow for 20 seconds. The horizontal axis in the histogram illustrated in FIG. 5 indicates a peak-to-peak interval time (second) while the vertical axis indicates the number of samples (N).

Referring to the example of FIG. 5, the peak-to-peak interval of 1.0 second has the most samples. Then, the peak-to-peak interval of 0.9 second has the next most samples. Therefore, referring to the example of FIG. 5, in the 20-second window having a change in blood flow, one pulse per 1.0 second is the most, and one pulse per 0.9 second is the next.

Figure 6:
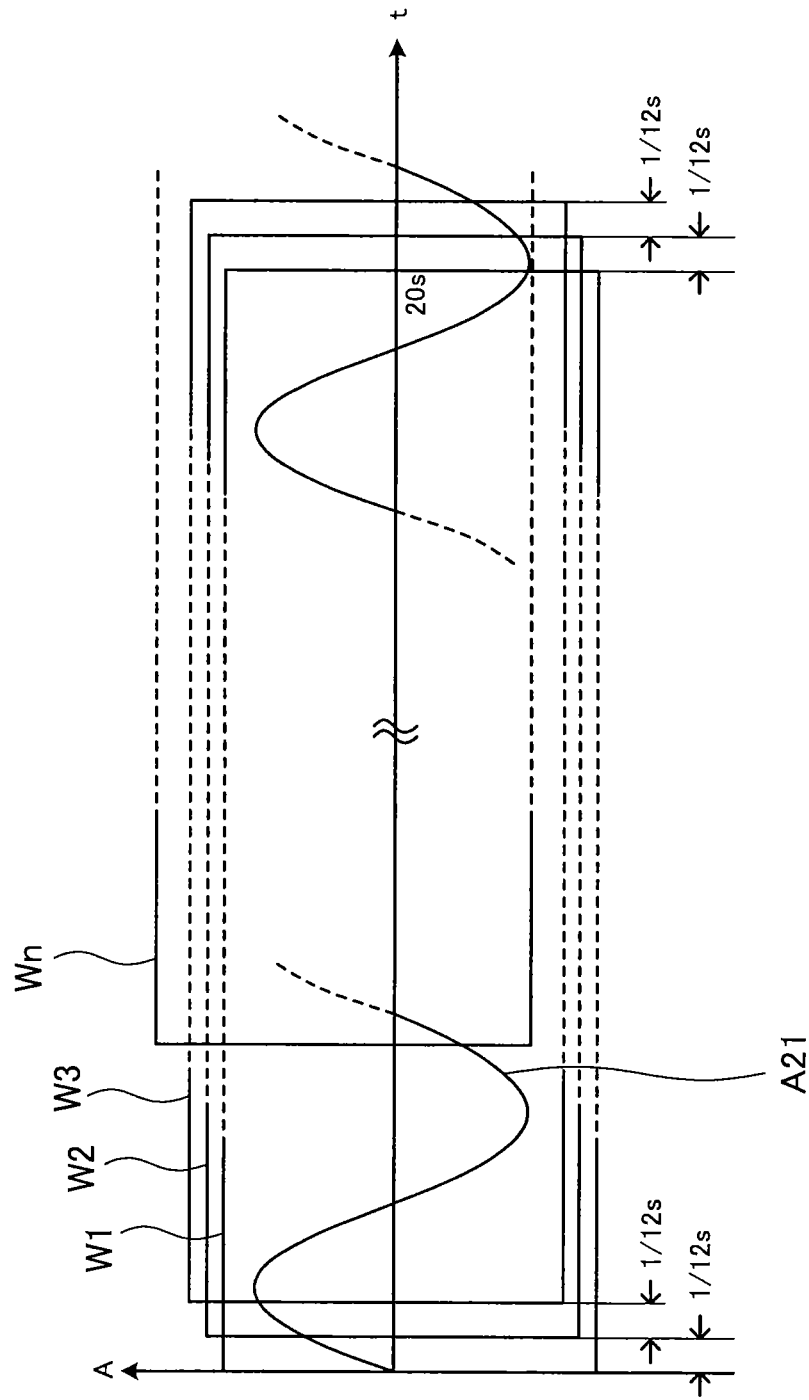
FIG. 6 is a diagram explaining a window.

FIG. 6 is a diagram explaining a window. The waveform A21 illustrated in FIG. 6 represents a change in blood flow calculated by the pulse rate calculator 22. Each of the windows W1, W2, W3, ..., Wn illustrated in FIG. 6 is a window for which the pulse rate calculator 22 creates a histogram of peak-to-peak intervals. The horizontal axis in FIG. 6 indicates time (seconds) while the vertical axis indicates amplitude (A) of blood flow.

Each window W1, W2, W3, ..., Wn covers 20 seconds for which a histogram of peak-to-peak intervals is created. The windows W1, W2, W3, ..., Wn are switched from one to another every $1/12$s if the frame rate of image data is set to 12 fps.

However, during the first 20 seconds after measurement of a pulse rate is started, the window W1 is not switched to the window W2. This is because, for the first 20 seconds, samples (image data) are not enough to obtain a change in blood flow (waveform A21) for the window W1. When image data is output from the camera module 21 immediately after (20+ $1/12$) seconds pass, the window is switched to the window W2. Then, the first image data obtained immediately after the measurement is started gets out of the window W2. It should be noted that the number of pieces of image data in each window W1, W2, W3, ..., Wn is 12×20.

The pulse rate calculator 22 calculates user's pulse rate per one minute from the created histogram. For example, it is assumed that the pulse rate calculator 22 creates a histogram of the window W2. The pulse rate calculator 22 calculates an average value of peak-to-peak intervals from the histogram. Then, the calculated average value is multiplied by 60 (seconds) to calculate user's pulse rate per one minute. However, the pulse rate calculator 22 takes peak-to-peak intervals with a predetermined number of samples or less as noise, and does not use these peak-to-peak intervals in calculating the average value. For example, the pulse rate calculator 22 takes peak-to-peak intervals of 0.2 second and 3.0 seconds as noise in FIG. 5, and therefore does not use these peak-to-peak intervals in calculating the average value.

The pulse rate calculator 22 calculates the user's pulse rate every 1/12 second which matches the frame rate (12 fps) of image data. In addition, as explained with reference to FIG. 6, during the first 20 seconds after the pulse rate measurement is started, samples are not enough to obtain a change in blood flow for the window W1. Therefore, a bell-shaped histogram illustrated in FIG. 5 is created because the number of samples of peak-to-peak intervals increases gradually. Therefore, since the number of samples for a histogram is small for the first several seconds in window W1, the average value of peak-to-peak intervals and the user's pulse rate which are calculated by the pulse rate calculator 22 have low accuracy.

The pulse rate calculator 22 outputs thus calculated user's pulse rate to the pulse application unit 24.

The number-of-steps detector 23 counts steps the user took for 1 minute. The number-of-steps detector 23 calculates the number of steps the user took for 1 minute from, for example, the count value of a pedometer.

The pulse application unit 24 receives the user's pulse rate from the pulse rate calculator 22, and receives the number of user steps counted for 1 minute from the number-of-steps detector 23.

The pulse application unit 24 has previously obtained user's pulse rate at rest, and stored it in the memory unit 26 such as a memory. The pulse rate at rest can be measured by the above-described camera module 21 and the pulse rate calculator 22, for example. To correctly measure and store a pulse rate at rest in the memory unit 26, the pulse rate at rest obtained after at least 20 seconds pass is stored. As described above, samples enough for a histogram are obtained after 20 seconds pass after the pulse rate measurement is started. Once a pulse rate at rest is stored, it is not necessary to be updated frequently.

The pulse application unit 24 calculates user's exercise intensity by using the number of user steps received from the number-of-steps detector 23. The pulse application unit 24 consults the exercise intensity TB 25 and obtains a coefficient based on the calculated exercise intensity.

FIG. 7 illustrates an example data structure of the exercise intensity TB. As illustrated in FIG. 7, the exercise intensity TB 25 has columns for exercise intensity (unit: METs) and coefficient. The exercise intensity column contains exercise intensity and the coefficient column contains a coefficient corresponding to the exercise intensity.

As described above, the pulse application unit 24 calculates user's exercise intensity by using the number of steps. The harder the user does exercise (the greater the number of user steps is), the higher the exercise intensity becomes.

As illustrated in FIG. 7, the coefficient value becomes larger in proportion to exercise intensity. If the user does hard exercise, the pulse application unit 24 obtains a large coefficient from the exercise intensity TB 25.

The pulse application unit 24 multiplies the user's pulse rate at rest, which is stored in the memory unit 26, by a coefficient obtained from the exercise intensity TB 25. That is, the user's pulse rate at rest is corrected according to the user's exercise. If the user does hard exercise, the pulse rate at rest is greatly corrected.

The pulse application unit 24 calculates user's pulse rate with the following equation (1) based on the user's pulse rate at rest corrected by using the exercise intensity TB 25 and the pulse rate calculated by the pulse rate calculator 22.

$$Pd = \{n \times Pr + (10-n) \times P'\}/10 \quad (1)$$

Pd is user's pulse rate to be displayed on the display unit 12 of the electronic device 10. Pr is user's pulse rate calculated by the pulse rate calculator 22. That is, Pr is user's pulse rate obtained from the user placing his fingertip on the camera 11.

P' is a pulse rate obtained by correcting the user's pulse rate at rest, which has been previously stored, according to user's exercise. That is, the corrected pulse rate P' is a pulse rate (P'=P×e) obtained by multiplying the pulse rate at rest P, which has been stored in the memory unit 26, by the coefficient e obtained from the exercise intensity TB 25.

n is an integral number of $1 \leq n \leq 10$, for example, and is incremented from the initial value 1 to value 10 every second.

In accordance with the equation (1), the user's pulse rate Pd is calculated while changing a ratio (weighting) of Pr to P', and is displayed on the display unit 12 of the electronic device 10.

FIG. 8 is a diagram explaining user' pulse rate to be displayed on the display unit of the electronic device. FIG. 8 illustrates a ratio of Pr to P' which is set for each second.

At the first 1 second after the pulse rate measurement is started, which means n=1, in the equation (1) where a pulse rate Pd to be displayed to the user is obtained, the ratio of Pr to P' is "1:9". At 2 seconds after the start, n=2 is obtained, and therefore the ratio of Pr to P' is "2:8". At 3 seconds from the start, n=3 is obtained, and therefore the ratio of Pr to P' is "3:7". Similarly, at 10 seconds from the start, n=10 is obtained, and therefore the ratio of Pr to P' is "10:0".

Immediately after the pulse rate measurement is started, samples are not enough for a histogram as described above. This means that the user's pulse rate calculated by the pulse rate calculator 22 has low accuracy. Therefore, the pulse application unit 24 calculates user's pulse rate Pd by setting the ratio of user's pulse rate calculated by the pulse rate calculator 22 to the pulse rate at rest corrected according to exercise intensity to "1:9", and displays it on the display unit 12.

As time passes, more samples are obtained for the histogram. When 10 seconds pass, the pulse application unit 24 sets the ratio of the user's pulse rate calculated by the pulse rate calculator 22 to the pulse rate at rest corrected according to the exercise intensity to "10:0", calculates user's pulse rate Pd, and displays it on the display unit 12. Thereafter, the pulse application unit 24 displays user's pulse rate calculated by the pulse rate calculator 22 on the display unit 12.

As described above, when the pulse rate measurement is started, the pulse application unit 24 corrects previously stored user's pulse rate at rest according to user's exercise intensity, and displays it on the display unit 12 of the electronic device 10. When the accuracy of calculation of a pulse rate via the camera 11 gets higher as time passes, the ratio of the pulse rate is set higher, and the pulse rate is displayed on the display unit 12. Thereby, the user can know a pulse rate with high accuracy immediately after starting to measure a pulse rate.

Figure 9:
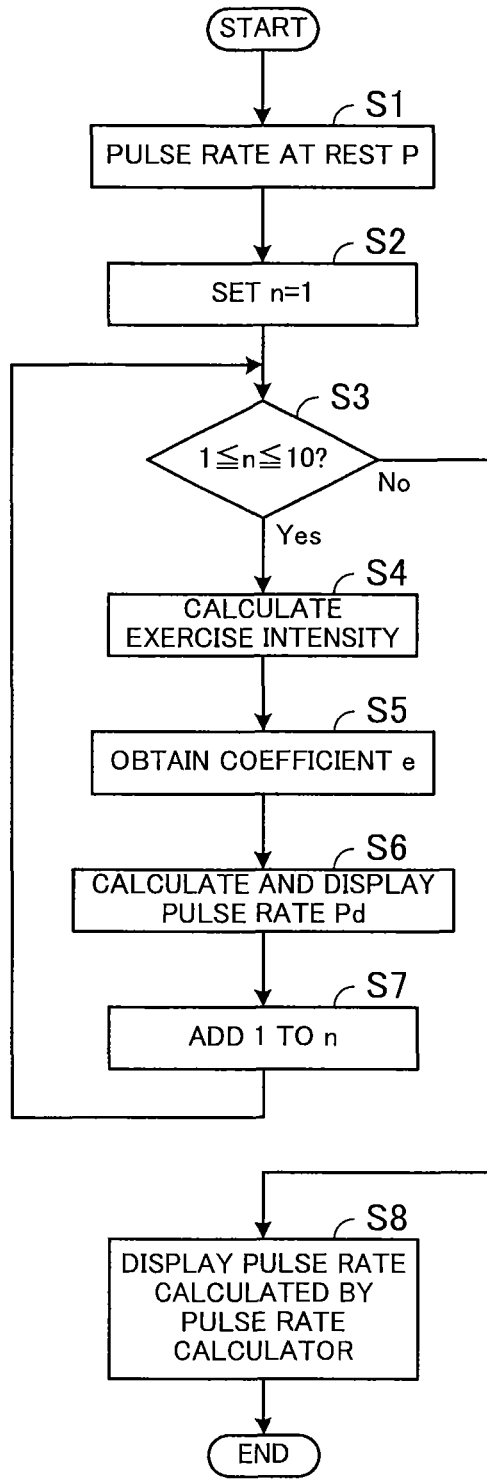
FIG. 9 is a flowchart of the operation of the electronic device.

FIG. 9 is a flowchart of the operation of the electronic device. At step S1, the pulse application unit 24 receives and stores user's pulse rate at rest P in the memory unit 26.

At step S2, the pulse application unit 24 starts to measure use's pulse rate and sets n in the equation (1) to "1".

At step S3, the pulse application unit 24 determines whether n is equal to or greater than 1 and is equal to or smaller than 10. If yes, the process goes on to step S4. If not, the process goes on to step S8.

At step S4, the pulse application unit 24 obtains the number of user steps calculated by the number-of-steps detector 23. The pulse application unit 24 calculates the user's exercise intensity based on the obtained number of user steps.

At step S5, the pulse application unit 24 consults the exercise intensity TB 25 to obtain a coefficient e corresponding to the user's exercise intensity calculated at step S4.

At step S6, the pulse application unit 24 calculates corrected user's pulse rate P'=P×e from the previously stored user's pulse rate at rest P and the coefficient e obtained at step S5. In addition, the pulse application unit 24 obtains the user's pulse rate Pr calculated by the pulse rate calculator 22 via the camera 11. The pulse application unit 24 calculates Pd to be displayed on the display unit 12 of the electronic device 10 with the equation (1) based on the calculated P' and Pr.

At step S7, the pulse application unit 24 adds "1" to n and the process goes back to step S3.

At step S8, the pulse application unit 24 displays the pulse rate output from the pulse rate calculator 22 on the display unit 12. That is, after 10 seconds pass, the pulse application unit 24 displays the pulse rate output from the pulse rate calculator 22 on the display unit 12.

As described above, after starting to measure a pulse rate, the electronic device 10 corrects the previously stored user's pulse rate at rest according to the user's exercise intensity, and displays it on the display unit 12. Then, when the user's pulse rate calculated via the camera 11 becomes accurate enough as time passes, the electronic device 10 sets the ratio of the pulse rate high, and displays the pulse rate on the display unit 12. Thereby, the electronic device 10 is capable of displaying a pulse rate with high accuracy even immediately after starting to measure the pulse rate. Thus, the user can know his pulse rate with high accuracy immediately after starting to measure the pulse rate.

It should be noted that in the above example, the user's blood flow is measured by using the camera 11, but this should not be limited thereto. For example, a change in user's blood flow may be obtained by, for example, a sensor comprising a Light Emitting Diode (LED) and a Photo Diode (PD), and his pulse rate may be calculated.

Now, the second embodiment will be described in details with reference to the accompanying drawings. Some electronic devices such as mobile telephones and pulse meters are not provided with a pedometer. The second embodiment will be described for an electronic device without a pedometer.

The appearance of the electronic device 10 in the second embodiment is the same as that illustrated in FIG. 2, and is provided with a camera 11 and a display unit 12. The block diagram of the electronic device 10 can be considered to have only a camera module 21, a pulse rate calculator 22, a pulse application unit 24, and a memory unit 26 because the electronic device 10 has no pedometer and therefore does not have the number-of-steps detector 23 and the exercise intensity TB 25 illustrated in FIG. 3.

The camera module 21 and the pulse rate calculator function in the same way as those of the first embodiment.

The functions of the pulse application unit 24 partially differ from those described in the first embodiment. The pulse application unit 24 calculates a pulse rate to be displayed on the display unit 12, without correcting user's pulse rate at rest previously stored in the memory unit 26. The pulse application unit 24 calculates a pulse rate Pd to be displayed on the display unit 12 with the following equation (2).

$$Pd = \{n \times Pr + (10-n) \times P\}/10 \quad (2)$$

Pd is user's pulse rate to be displayed on the display unit 12 of the electronic device 10.

Pr is user's pulse rate calculated by the pulse rate calculator 22. That is, Pr is user's pulse rate obtained from the user putting his fingertip on the camera 11.

P is previously stored user's pulse rate at rest.

n is an integral number of $1 \leq n \leq 10$, for example, and is incremented from the initial value 1 to value 10 every second.

The equation (2) uses P as it is, which is different from the equation (1). In the first embodiment, the exercise intensity is obtained from the number of user steps, and therefore P is corrected by P'=P×e. In the second embodiment, P is not corrected but is used as it is.

Figure 10:
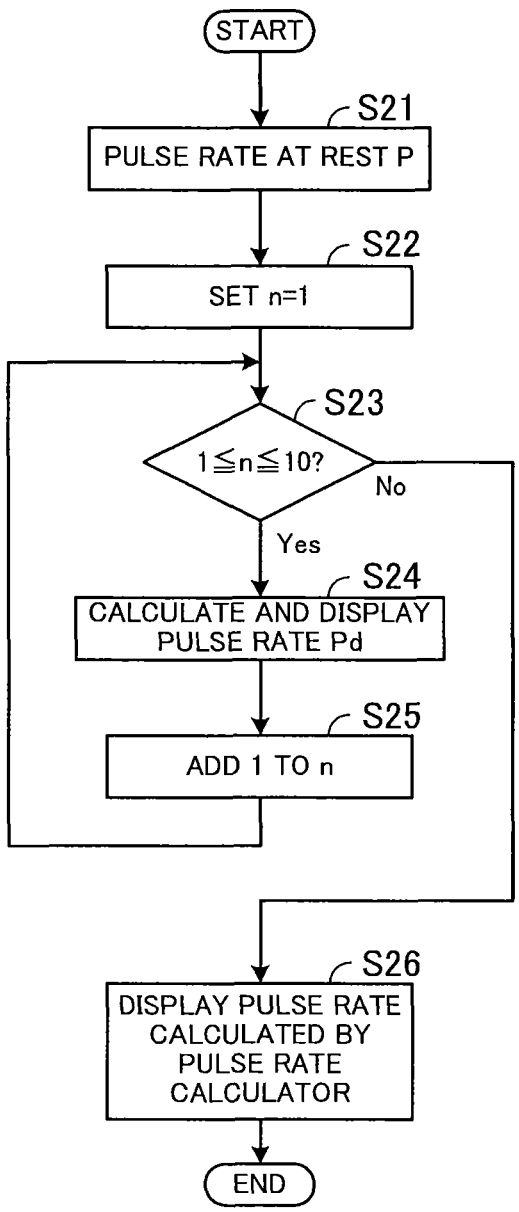
FIG. 10 is a flowchart of the operation of an electronic device according to the second embodiment.

FIG. 10 is a flowchart of the operation of the electronic device according to the second embodiment. At step S21, the pulse application unit 24 previously accepts and stores user's pulse rate at rest P in the memory unit 26.

At step S22, the pulse application unit 24 begins to measure user's pulse rate and sets n of the equation (2) to "1".

At step S23, the pulse application unit 24 determines whether n is equal to or greater than 1 and equal to or smaller than 10. If yes, the process goes on to step S24. If not, the process goes on to step S26.

At step S24, the pulse application unit 24 obtains previously stored user's pulse rate at rest from the memory unit 26. In addition, the pulse application unit 24 obtains user's pulse rate Pr calculated by the pulse rate calculator 22 via the camera 11. The pulse application unit 24 calculates Pd to be displayed on the display unit 12 of the electronic device 10 with the equation (2) based on the obtained P and Pr.

At step S25, the pulse application unit 24 adds "1" to n, and the process goes back to step S23.

At step S26, the pulse application unit 24 displays the pulse rate output from the pulse rate calculator 22 on the display unit 12. That is, after 10 seconds pass, the pulse application unit 24 displays the pulse rate output from the pulse rate calculator 22 on the display unit 12.

As described above, in the case where the electronic device 10 has no function of calculating exercise intensity, like a pedometer, it displays the user's pulse rate at rest previously stored in the memory unit 26 on the display unit 12. Then, when the user's pulse rate is calculated via the camera 11 with high accuracy as time passes, the electronic device 10 sets the ratio of the pulse rate higher, and displays the pulse rate on the display unit 12. In this way, the electronic device 10 is capable of displaying a pulse rate with high accuracy on the display unit 12 immediately after starting to measure the pulse rate.

Now the third embodiment will be described with reference to the accompanying drawings. If a user in the sun moves into a shade or the user in a shade moves in the sun while measuring his pulse rate by using a camera, for example, the pulse rate which is displayed on the display unit may greatly vary due to a change in light source (in this case, the sun light). The third embodiment is designed to suppress a rapid change (noise) in pulse rate in steady state (after pulse rate calculation while changing a change in the ratio is finished, that is, after 10 seconds pass).

The appearance of the electronic device 10 according to the third embodiment is the same as that illustrated in FIG. 2. The electronic device 10 has a camera 11 and a display unit 12. The block diagram of the electronic device 10 is the same as that illustrated in FIG. 3. However, the functions of the pulse application unit 24 are partly different.

In steady state, the pulse application unit 24 displays the pulse rate output received from the pulse rate calculator 22 on the display unit 12. At this time, the pulse application unit 24 displays the pulse rate while suppressing a rapid change. That is, in the third embodiment, a process of suppressing a rapid change is added to the process of step S8 of FIG. 9.

In steady state, when the pulse application unit 24 receives a pulse rate from the pulse rate calculator 22, it calculates a difference between a previously corrected pulse rate and the pulse rate (currently measured pulse rate) received from the pulse rate calculator 22 this time, in accordance with the following equation (3) to thereby calculate a change in pulse rate.

$$[\text{change in pulse rate}]=[\text{currently measured pulse rate}]-[\text{previously corrected pulse rate}] \quad (3)$$

If the change in pulse rate exceeds a predetermined value, the pulse application unit 24 adds the previously corrected pulse rate and the currently measured pulse rate, divides the resultant by two to thereby calculate a corrected pulse rate (currently corrected pulse rate), in accordance with the following equation (4).

$$[\text{currently corrected pulse rate}]=([\text{previously corrected pulse rate}]+[\text{currently measured pulse rate}])/2 \quad (4)$$

That is, if a change in pulse rate calculated by the equation (3) exceeds the predetermined value, the pulse application unit 24 calculates and displays an average of the previously corrected pulse rate and the currently measured pulse rate in accordance with the equation (4) on the display unit 12. If the change in pulse rate does not exceed the predetermined value, on the other hand, the pulse application unit 24 displays the currently measured pulse rate received from the pulse rate calculator 22 on the display unit 12. The pulse application unit 24 truncates decimal numbers of the corrected pulse rate.

FIG. 11 is a diagram explaining how to correct a pulse rate according to the third embodiment. In FIG. 11, a column for time of display contains the number of times a pulse rate is displayed on the display unit 12. A column for measured pulse rate contains a pulse rate calculated by the pulse rate calculator 22. A column for corrected pulse rate contains a pulse rate corrected by the pulse application unit 24. A column for displayed pulse rate contains a pulse rate that the pulse application unit 24 displays on the display unit Referring to FIG. 11, it is assumed that at the first time, the pulse application unit 24 receives a pulse rate of "80" from the pulse rate calculator 22. The pulse rate application unit 24 takes the received pulse rate of "80" as a corrected pulse rate. In addition, the pulse application unit 24 displays the corrected pulse rate of "80" on the display unit 12 and stores it in the memory unit 26.

Then, it is assumed that, at the second time, the pulse application unit 24 receives a pulse rate of "90" from the pulse rate calculator 22. The pulse application unit 24 calculates a change in pulse rate in accordance with the equation (3). In this example of FIG. 11, a change in pulse rate is 90−80=10.

If the change in pulse rate is equal to or greater than a predetermined value, the pulse application unit 24 calculates a corrected pulse rate in accordance with the equation (4). In this case, it is assumed that, if a change in pulse rate is equal to or greater than 10, a corrected pulse rate is calculated. In the example of FIG. 11, a change in pulse rate is "10" as described above, and therefore the pulse application unit 24 adds the previously corrected pulse rate "80" and the currently measured pulse rate "90", and divides the resultant by 2 to thereby calculate a currently corrected pulse rate "85", as indicated in the corrected pulse rate column at the second time. The pulse application unit 24 displays the calculated currently amended pulse rate "85" on the display unit 12, and stores it in the memory unit 26.

It is assumed that, at the third time, the pulse application unit 24 receives a pulse rate of "99" from the pulse rate calculator 22. The pulse application unit 24 calculates a change in pulse rate in accordance with the equation (3). In the example of FIG. 11, a change in pulse rate is 99−85=14.

The pulse application unit 24 calculates a corrected pulse rate in accordance with the equation (4) since the change in pulse rate is greater than "10". In the example of FIG. 11, the pulse application unit 24 adds the previously corrected pulse rate "85" and the currently measured pulse rate "99", and divides the resultant by 2 to thereby calculate a currently corrected pulse rate "92", as indicated in the corrected pulse rate column at the third time. The pulse application unit 24 displays the calculated currently corrected pulse rate "92" on the display unit 12, and stores it in the memory unit 26.

It is assumed that, at the fourth time, the pulse application unit 24 receives a pulse rate of "100" from the pulse rate calculator 22. The pulse application unit 24 calculates a change in pulse rate in accordance with the equation (3). In this example of FIG. 11, the change in pulse rate is calculated as 10−92=8.

As the change in pulse rate is smaller than "10", the pulse application unit 24 displays the pulse rate "100" received from the pulse rate calculator 22 on the display unit 12 without correcting it, and stores it in the memory unit 26.

Figure 12:
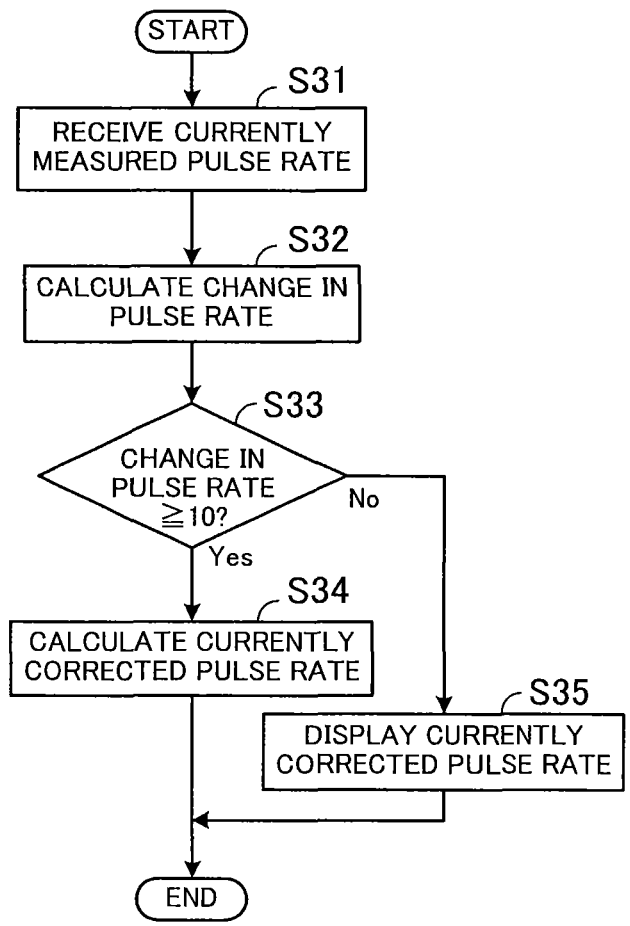
FIG. 12 is a flowchart of a correction process to be performed when the electronic device is in steady state.

FIG. 12 is a flowchart illustrating a correction process to be performed when the electronic device is in steady state. At step S31, the pulse application unit 24 receives a currently measured pulse rate from the pulse rate calculator 22.

At step S32, the pulse application unit 24 calculates a difference between the currently measured pulse rate and the previously corrected pulse rate stored in the memory unit 26 according to the equation (3) to calculate a change in pulse rate.

At step S33, the pulse application unit 24 determines whether the change in pulse rate is equal to or greater than 10. If yes, the process proceeds to step S34. If not, the process proceeds to step S35.

At step 34, the pulse application unit 24 calculates a currently corrected pulse rate in accordance with the equation (4). The pulse application unit 24 displays the calculated currently corrected pulse rate on the display unit 12, and stores it in the memory unit 26.

At step S35, the pulse application unit 24 displays the currently measured pulse rate received from the pulse rate calculator 22 on the display unit 12, and stores it in the memory unit 26.

As described above, the electronic device 10 in steady state displays a pulse rate on the display unit 12 while suppressing a rapid change in pulse rate. This makes it possible to suppress a rapid change in pulse rate which is taken as noise caused due to a change in light source or the like.

The processing functions described above can be realized by using a program. In this case, the program describing the processing contents of the functions that the electronic device 10 needs to have may be recorded on a portable recording medium such as a Compact Disk Read Only Memory (CD-ROM) or a flexible disk, which may be then distributed. The program may be stored in a memory of a computer connected via a network and is transferred to the electronic device 10 via the network. The electronic device 10 can realize the above-described processing functions by executing the program stored in the memory.

The disclosed electronic device and pulse rate calculating method can realize displaying a pulse rate with high accuracy immediately after starting to measure the pulse rate.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present invention have been described in detail, it should be understood that various changes, substitutions, and alterations could be made thereto without departing from the spirit and scope of the invention.

What is claimed is:

1. A non-transitory computer-readable recording medium storing a pulse rate calculating program for displaying a user's pulse rate, the pulse rate calculating program causing a computer to perform as:

a pulse rate measuring unit which measures the user's current pulse rate;

a pulse rate memory unit which stores the user's previous pulse rate; and a pulse rate calculator which calculates the user's pulse rate by calculating a weighted mean while changing a weighted ratio of both a first weight afforded to the user's current pulse rate measured by the pulse rate measuring unit and a second weight afforded to the user's previous pulse rate stored in the pulse rate memory unit;

wherein the pulse rate calculator calculates the user's pulse rate by setting the second weight higher than the first weight at the time of starting the rate calculation and then by gradually increasing the first weight over time, and wherein the pulse rate calculator outputs the calculated user's current pulse rate as the user's pulse rate when a predetermined period of time passes after starting the measurement.

* * * * *